(12) United States Patent
Kroll et al.

(10) Patent No.: US 6,579,915 B2
(45) Date of Patent: Jun. 17, 2003

(54) RADIATION CURABLE ADHESIVE COMPOSITIONS COMPRISING BLOCK COPOLYMERS HAVING VINYL FUNCTIONALIZED POLYDIENE BLOCKS

(75) Inventors: Mark S. Kroll, Arden Hills, MN (US); Margarita Acevedo, Minneapolis, MN (US); Janelle C. Cameron, Mendota Heights, MN (US); Thomas F. Kauffman, Harleysville, PA (US); Jeffrey S. Lindquist, Maple Grove, MN (US); Eugene R. Simmons, Vadnais Heights, MN (US); David B. Malcolm, Maplewood, MN (US); Kathryn A. Coleman, Minneapolis, MN (US)

(73) Assignee: H.B. Fuller Licensing & Financing Inc., St. Paul, MN (US)

( * ) Notice: Subject to any disclaimer, the term of this patent is extended or adjusted under 35 U.S.C. 154(b) by 0 days.

(21) Appl. No.: 09/771,764

(22) Filed: Jan. 29, 2001

(65) Prior Publication Data

US 2002/0016381 A1 Feb. 7, 2002

Related U.S. Application Data

(60) Provisional application No. 60/179,263, filed on Jan. 31, 2000.

(51) Int. Cl.$^7$ .................................................. C08F 2/46
(52) U.S. Cl. ...................... 522/109; 522/110; 522/111; 522/112; 524/500; 524/502; 524/505; 524/270; 524/274; 526/931; 526/935
(58) Field of Search ................................ 524/505, 274, 524/270, 500, 502; 526/931, 935; 522/109, 110, 111, 112

(56) References Cited

U.S. PATENT DOCUMENTS

| | | | |
|---|---|---|---|
| 4,181,752 A | | 1/1980 | Martens et al. ............ 427/54.1 |
| 4,329,384 A | | 5/1982 | Vesley et al. .................. 428/40 |
| 4,533,566 A | | 8/1985 | Evans .......................... 427/44 |
| 4,780,367 A | * | 10/1988 | Lau et al. ............... 428/355 BL |
| 5,093,406 A | * | 3/1992 | Lossner et al. ........ 428/355 BL |
| 5,300,582 A | * | 4/1994 | Debier et al. ................ 525/314 |
| 5,332,876 A | * | 7/1994 | Romano et al. ....... 200/61.45 R |
| 5,382,604 A | | 1/1995 | Erickson ...................... 522/158 |
| 5,576,395 A | * | 11/1996 | Spence et al. ............... 525/105 |
| 5,614,577 A | * | 3/1997 | Sasaki et al. .......... 428/355 BL |
| 5,662,758 A | | 9/1997 | Hamilton et al. ............ 156/221 |
| 5,705,551 A | * | 1/1998 | Sasaki et al. ................ 524/271 |
| 5,719,226 A | | 2/1998 | Kegley ........................ 524/505 |
| 5,773,506 A | | 6/1998 | Nestegard et al. |
| 5,804,663 A | | 9/1998 | De Craene et al. ......... 525/314 |
| 5,891,957 A | | 4/1999 | Hansen et al. |
| 5,932,648 A | | 8/1999 | Troska et al. ................ 524/505 |

FOREIGN PATENT DOCUMENTS

WO  00 22062  4/2000

OTHER PUBLICATIONS

"Rubber–based Radiation Curable Pressure Sensitive Adhesives", Martine Dupont, et al., Nov. 1999, 7 pages.

"UV Crosslinkable Styrenic Block Copolymers . . . A Door to High Temperature Resistant Hot Melt Adhesive Applications" Martine Dupont, the Journal of the Adhesive and Sealent Council, Inc., 1997 Spring Convention, Pittsburgh, Pennsylvania, Mar. 23–26, pp. 229–240.

* cited by examiner

Primary Examiner—James J. Seidleck
Assistant Examiner—Sanza L. McClendon

(57) ABSTRACT

The invention is directed to a radiation curable adhesive composition comprising at least one vinyl modified block copolymer having a first polyvinyl aromatic block and a second polydiene block having vinyl functionality, and at least one tackifier. Optionally, the composition may comprises at least one second block copolymer that has not been vinyl modified, at least one platicizer, and at least one wax. The invention is also directed to a double-faced label formed from the composition and the method of producing said label.

43 Claims, 4 Drawing Sheets

RADIATION CURABLE ADHESIVE COMPOSITIONS COMPRISING BLOCK COPOLYMERS HAVING VINYL FUNCTIONALIZED POLYDIENE BLOCKS

This application claims benefit of U.S. provisional patent application Ser. No. 60/179,263 filed Jan. 31, 2000.

FIELD OF THE INVENTION

The present invention relates to a radiation curable adhesive composition comprising at least one vinyl modified block copolymer having polyvinyl aromatic (styrenic) endblocks and polydiene midblocks having vinyl functionality. The adhesive composition exhibits at least one of a variety of improved adhesive performance characteristics depending on the type and amount of the ingredients selected.

BACKGROUND OF THE INVENTION

"UV Crosslinkable Styrenic Block Copolymers . . . A Door to High Temperature Heat Resistant Hot Melt Adhesive Applications" by Martine Dupont, the Journal of the Adhesive and Sealent Council, Inc., 1997 Spring Convention, Pittsburgh, Pa. Mar. 23–26, 1997, pp 229–240, discloses compositions containing 25 to 35 wt-% of a block copolymer KX-222C, a solid hydrogenated tackifying resin Regalite R91 or MBG 264, a hydrogenated liquid resin Regalrez 1018, a photoinitiator Irgacure 651 and an antioxidant Irganox 1010. The composition exhibits the lowest viscosity of 10 Pa.s at 160° C.

U.S. Pat. No. 5,804,663 discloses radiation sensitive vinyl aromatic block copolymers and radiation curable adhesives, sealants, and coatings containing such block copolymers. The radiation sensitive block copolymers contain at least one block derived from vinyl aromatic monomer and at least one block derived from butadiene. The adhesive exhibits the lowest viscosity of 6.7 Pa.s at 160° C.

SUMMARY OF THE INVENTION

In one embodiment, the invention is directed to a radiation curable adhesive composition that is amenable to being applied at a low application temperature, i.e., an application temperature no greater than about 150° C. Preferably, the application temperature is no greater than about 140° C. and more preferably, no greater than about 130° C. The adhesive composition comprises from about 10 wt % to about 40 wt %, of at least one vinyl modified block copolymer having polyvinyl aromatic (styrenic) endblocks and vinyl functionalized polydiene midblocks, and from about 20 wt % to about 90 wt % of at least one tackifier. The vinyl functionality of the polydiene block presents reactively favorable sites and is at a sufficient concentration such that the block copolymer crosslinks substantially through the vinyl functionality upon exposure to radiant energy. The adhesive composition may further comprise at least one plasticizer. Preferably, from about 30 wt % to about 90 wt % of the ingredients comprised of the composition are liquids at ambient temperature. Preferably, the liquid ingredients comprise a mixture of at least one polydiene block compatible tackifier and at least one polyvinyl aromatic block compatible plasticizer. The adhesive composition may further comprise up to about 40 wt %, preferably from about 5 wt % to about 40 wt %, more preferably from about 5 wt % to about 20 wt %, of at least one second polymer such that the total polymer content in the composition is at least about 15 wt %. The second polymer may also be radiation sensitive, i.e., able to substantially crosslink upon exposure to radiant energy, or may not be radiation sensitive. The adhesive composition has a Brookfield viscosity of less than about 10,000 cps and preferably, less than about 6,000 cps at a temperature of about 160° C.

In another embodiment, the invention is directed to a radiation curable adhesive composition comprising from about 10 wt % to about 40 wt % at least one vinyl modified block copolymer having at least two blocks, wherein the first block is a polyvinyl aromatic block and the second block is a polydiene block having vinyl functionality, from about 10 wt % to about 80 wt % of at least one tackifier that is compatible with the polydiene block; and from about 10 wt % to about 40 wt % of at least one plasticizer. The plasticizer is preferably a polyvinyl aromatic block compatible plasticizer having softening point of no greater than 100° C.; a high molecular weight polydiene block compatible plasticizer having a weight average molecular weight of no less than about 20,000 g/mol, preferably, up to about 100,000 g/mol, such as polyisoprene, or mixtures thereof.

In yet another embodiment, the invention is directed to a radiation curable adhesive composition comprising from about 10 wt % to about 40 wt % of at least one vinyl modified block copolymer having at least two blocks, wherein the first block is a polyvinyl aromatic block and the second block is a polydiene block having vinyl functionality; from about 5 wt % to about 40 wt % of at least one second polymer selected from the group consisting of styrenic block copolymers, ethylene/α-olefin interpolymers, amorphous polyalphaolefins, interpolymers of ethylene, and mixtures thereof, and from about 10 wt % to about 90 wt % of at least one tackifier.

In yet another embodiment, the invention is directed to a radiation curable adhesive composition comprising from about 10 wt % to about 50 wt % of at least one vinyl modified block copolymer having at least two blocks, wherein the first block is a polyvinyl aromatic block and the second block is a polydiene block having vinyl functionality; from about 20 wt % to about 55 wt % of at least one tackifier; from about 10 wt % to about 40 wt % of at least one wax; and from about 0 wt % to about 35 wt % of at least one plasticizer. The adhesive is not substantially tacky at a temperature of lower than the cloud point of the wax. The adhesive exhibits high shear resistance at high temperature, therefore, is appropriate for stretchable labels.

In yet another embodiment, the invention is directed to a double-faced tape formed from a single radiation curable adhesive composition, said double-faced tape having a first surface and a second opposing surface, said first surface exhibiting a first 180° peel value and said second surface exhibiting a second 180° peel value that is greater than said first peel value, upon radiation curing; and to a method of producing the double-faced tape comprising applying an adhesive composition onto a release-coated surface to form an adhesive film layer and curing the adhesive film such that the adhesive film exhibits different adhesive properties on one surface than the opposing surface.

In yet another embodiment, the invention is directed to a plastic wrap comprising a film and an adhesive composition disposed on one surface of said film, said adhesive composition exhibits a storage modulus (G') of less than about $1 \times 10^5$ dynes/cm$^2$ at about 25° C. Preferably, the storage modulus is within the pressure sensitive adhesive region as defined by the Dahlquist criteria through a temperature range of from about 0° C. to about 120° C.

In yet another embodiment, the invention is directed to a hook or loop substrate bonded with a radiation curable adhesive composition of the invention.

In yet another embodiment, the invention is directed to a disposable article having at least one substrate bonded with a radiation cured adhesive composition of the invention, wherein said adhesive composition is in contact with an oil-based skin care ingredient.

The adhesive compositions of the invention are amenable to a variety of end-uses, particularly for pressure sensitive adhesives for high performance tapes and labels such as freezer-grade tapes and labels, and automotive adhesives as well as for various adhesive applications wherein adhesion to wet surface is desired, such as medical products that employ an adhesive.

The radiation curable adhesive compositions can be formulated to exhibit higher peel values, higher heat resistance, improved cold temperature properties particularly at temperatures below 0° C., improved adhesion to wet surfaces and/or improved solvent and plasticizer resistance.

DETAILED DESCRIPTION OF THE INVENTION

Figure 1:
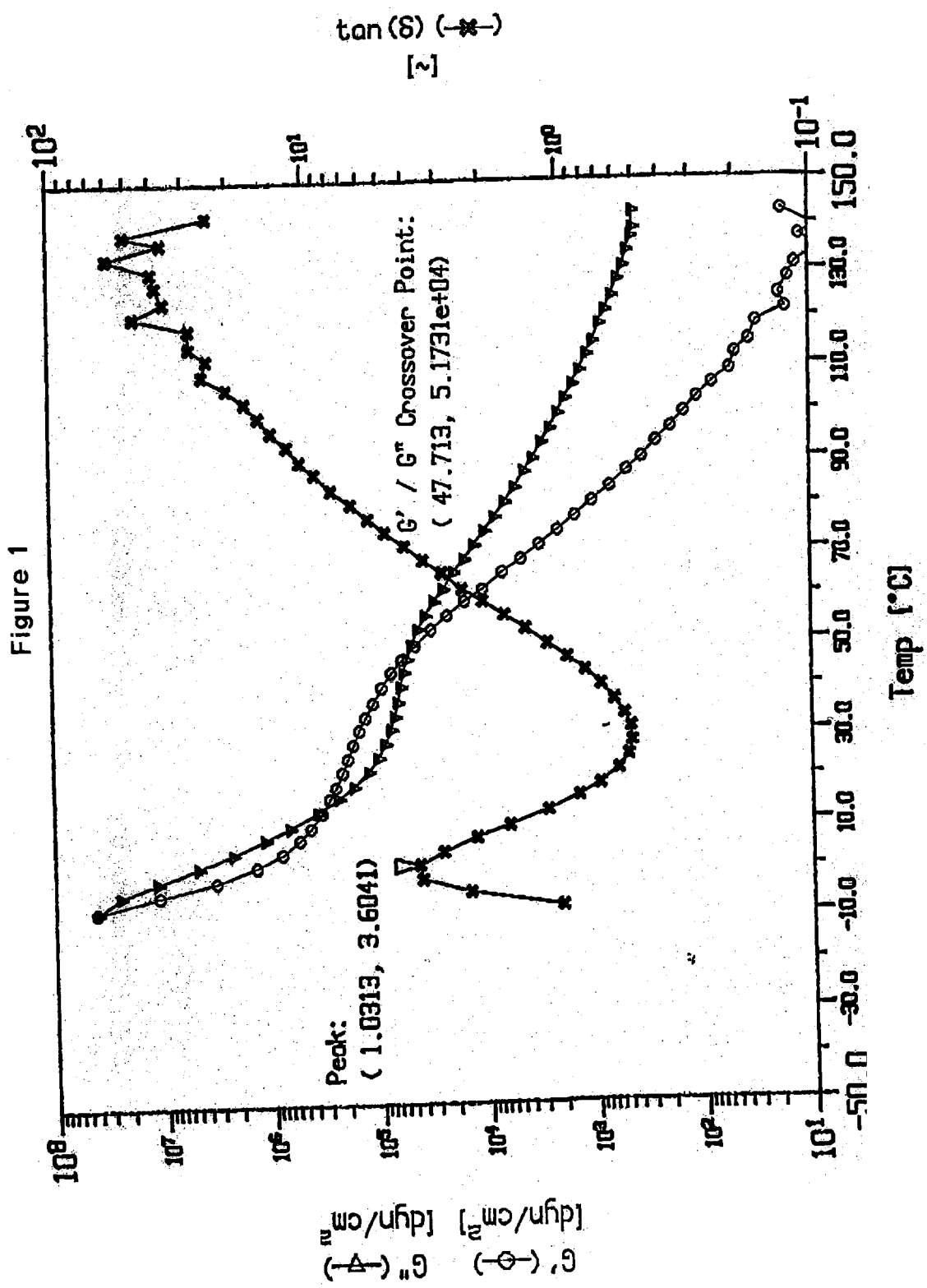
FIG. 1 represents the storage modulus (G'), loss modulus (G") and tan delta of the adhesive composition in Example 2 prior to curing.
Figure 2:
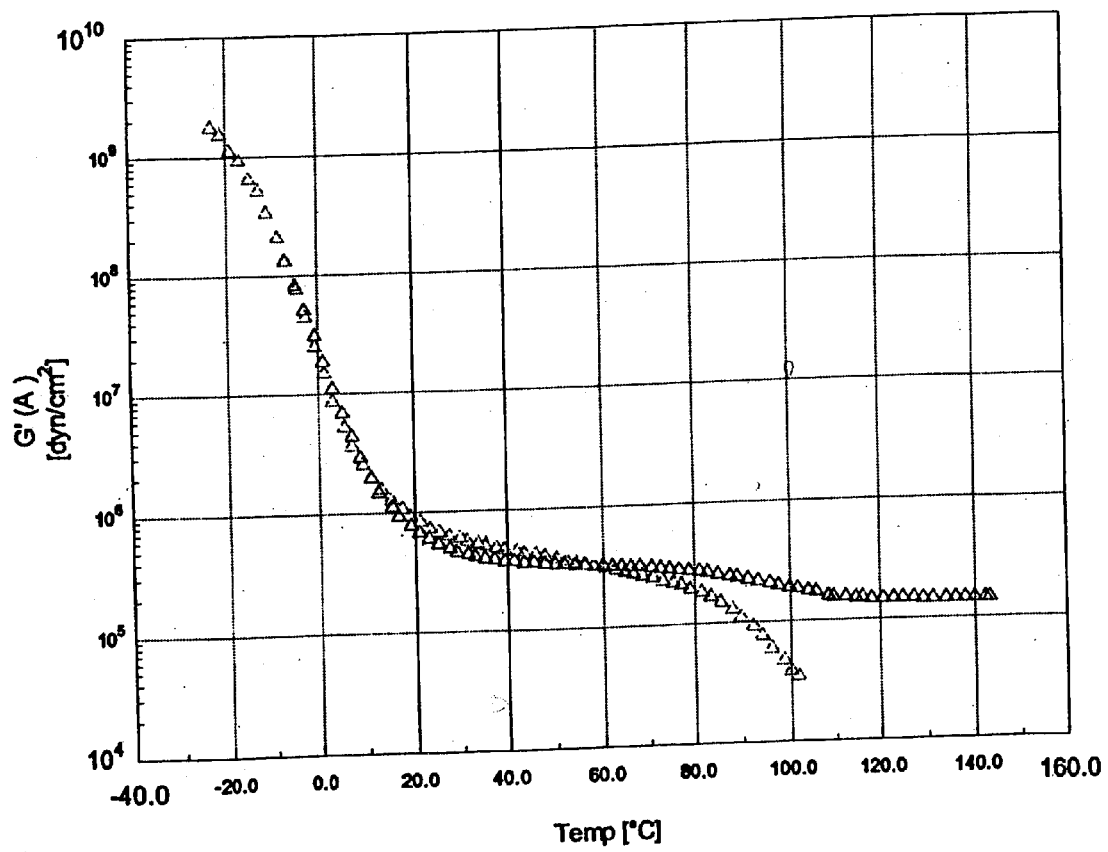
FIGS. 2 and 3 represent the storage modulus (G'), loss modulus (G") and tan delta of the adhesive compositions in Examples 6 and 20, respectively, prior to and after curing. The radiation induced crosslinking extends the storage modulus plateau. The rheogram of Example 2 after curing would demonstrate a similar effect.
Figure 3:
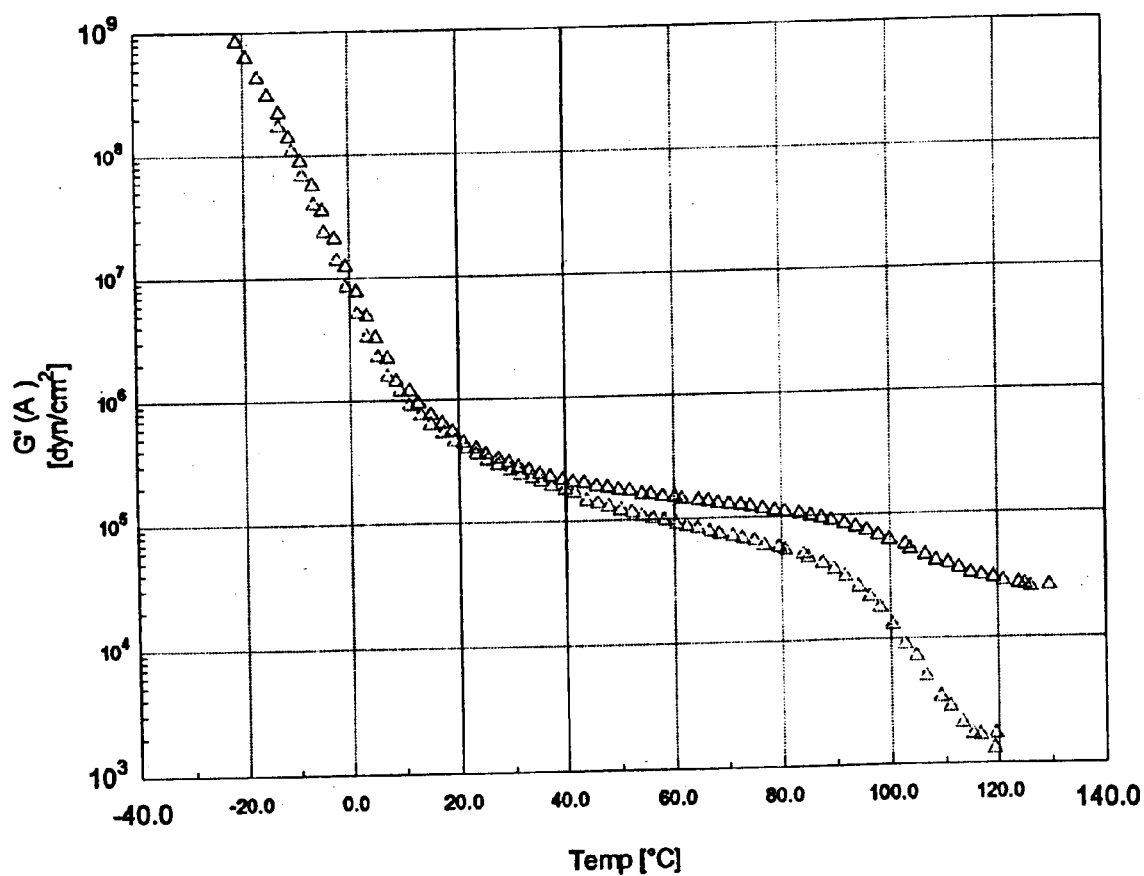
Figure 4:
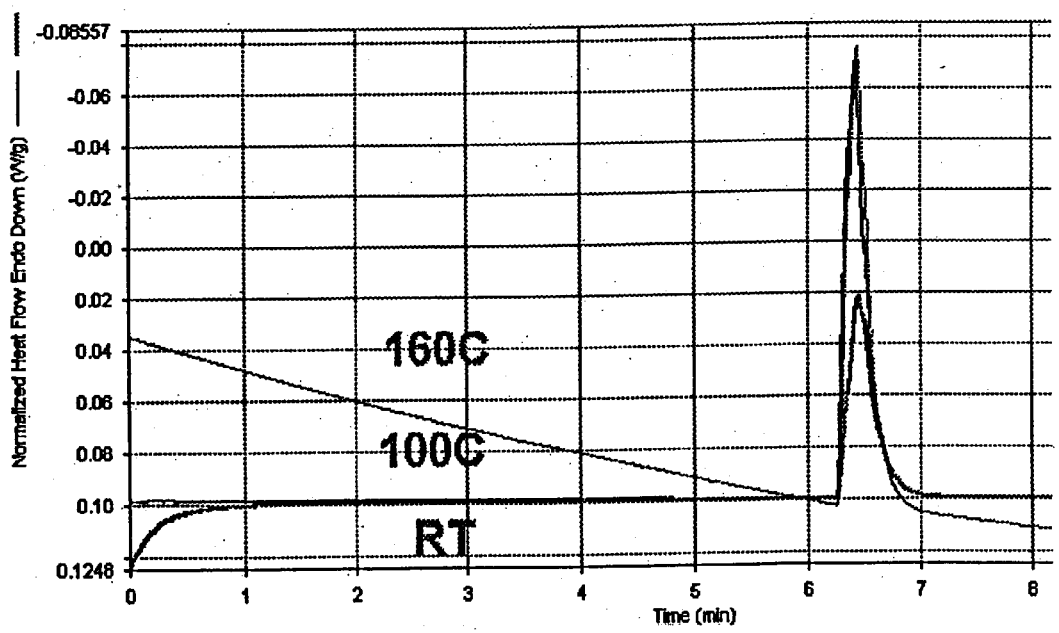
FIG. 4 depicts the curing exotherms of the adhesive composition in Example 6 at room temperature, 100° C. and 160° C., respectively. The area under the curve represents the extent of the reaction. Only a fraction of the reaction take place at room temperature in comparison to elevated temperatures. However, no significant differences were found by increasing the temperature above 100° C.

The radiation curable adhesive composition of the invention comprises at least one vinyl modified block copolymer, at least one tackifier and optionally, at least one plasticizer.

The vinyl modified block copolymer comprises at least two blocks wherein the first block is a polyvinyl aromatic (styrenic) endblock and the second block is a polydiene mid-block that has been 1,2-vinyl modified, i.e., the resultant 1,2-vinyl double bonds dangle on polydiene mid-blocks. These dangling double bonds, or the vinyl functionality, present reactively favorable sites and are at a sufficient concentration such that the vinyl modified block copolymer crosslinks substantially through such vinyl functionality upon exposure to a radiant energy source. The polyvinyl aromatic block in the vinyl modified block copolymer is typically styrene. However, various alkyl-substituted styrenes, alkoxy-substituted styrenes, vinyl napthalene, alkyl-substituted vinyl napthalenes and the like are also suitable compounds for formation of the polyvinyl aromatic block. The polydiene block may be formed from a variety of conjugated diolefins containing from about 4 to about 24 carbon atoms, such as those disclosed by U.S. Pat. No. 5,382,604, which is incorporated herein by reference. Typically, however, the conjugated diene is 1,3-butadiene and/or isoprene. The conjugated diene block is typically modified such that sufficient vinyl functionality is incorporated.

The structure of the vinyl modified block copolymer may be linear, multiblock, radial, multi-arm, or grafted in structure. Preferably, the vinyl modified block copolymer is a branched asymmetric molecule containing styrene-butadiene (SB) and homopolybutadiene arms having the general formula $(SB)_2B_2$ wherein the butadiene midblock has been 1,2-vinyl modified. Information concerning the synthesis, physical properties, compatibility with other ingredients, etc. is known from U.S. Pat. No. 5,804,663, incorporated herein by reference. The butadiene midblock cart include a vinyl content of from 25% by weight to 70% by weight, preferably from 45% by weight to 70% by weight. An example of vinyl modified block copolyiner is $(AB)_p(B^1)_qX$, wherein A is a poly(vinyl aromatic)block and B and $B^1$ are poly(butadiene)blocks, wherein X is the residue of a hexavalent coupling agent, p and q both have a number average value in the range of from 1.5 to 4.5, the sum of p and q is 6, the block copolymers have an average bound vinyl aromatic content in the range of from 10% by weight to 50% by weight, preferably from 10% by weight to 30% by weight, a total apparent molecular weight from 100,000 to 500,000, and a vinyl content in the polybutadiene blocks in the range of from 25% by weight to 70% by weight, preferably from 45% by weight to 70% by weight. Preferably p and q have both a number average value of from 2.8 to 3.2, or p and q have values from 1.8 to 2.2 and 3.8 to 4.2, respectively.

The A blocks in the block copolymers have in general an apparent molecular weight in the range of from 5,000 to 50,000, preferably from 7,000 to 20,000, most preferably from 9,000 to 15,000. The B and $B^1$ blocks in the block copolymers have an apparent molecular weight in the range from 15,000 to 250,000, preferably from 25,000 to 100,000. It will be appreciated that the respective B and $B^1$ blocks in a block copolymer may have the same or different molecular weight. The radiation sensitive block copolymers preferably have a total apparent molecular weight of from 200,000 to 350,000. The vinyl content in the poly(butadiene) ann blocks is preferably in the range of from 45% by weight to 70% by weight. A preferred $(SB)_2B_2$ block copolymer is commercially available from Shell under the tradename Kraton® D-KX-222C. Although vinyl modified block copolymers having homopolybutadiene arms are preferred, other vinyl modified styrene-butadiene-styrene (SBS) block copolymers such as vinyl modified random styrene-butadiene multiblock (S-B-S-B-S) block copolymers may also be employed provided that the polydiene midblock contains a sufficient concentration of the vinyl functionality that crosslink upon exposure to radiant energy. Alternative vinyl modified block copolymers that may be employed alone or in combination with Kraton® D-KX222C include, such as a vinyl modified random styrene-butadiene multi-block (S-B-S-B-S) block copolymer having vinyl content ranging from about 10 wt % to about 50 wt % sold under the trade designation SR-8272 and SR-8273 by Firestone.

The amount of the vinyl modified block copolymer employed may depend to some extent on the targeted end-use. Typically, the adhesive composition comprises from about 10 wt % to about 50 wt %, preferably from about 10 wt % to about 40 wt %, more preferably from about 10 wt % to about 30 wt % and even more preferably, from about 15 wt % to about 25 wt % of the vinyl modified block copolymer, based on the total weight of the composition.

The radiation curable adhesive composition of the invention also comprises at least one tackifier, i.e., any of the ingredients described below that are useful to shift the glass transition temperature (Tg) of the vinyl modified block copolymer to a higher temperature and impart tack to the adhesive composition. Tack is defined in ASTM D-1878-

61T as "the property of a material that enables it to form a bond of measurable strength immediately on contact with another surface". The amount of tackifier ranges from about 10 wt % to about 90 wt %, preferably, from about 10 wt % to about 80 wt %, based on the total weight of the adhesive composition. Preferably, the adhesive composition comprises at least about 20 wt %, more preferably, at least about 40 wt %, and most preferably, at least about 50 wt % tackifier.

In general, useful tackifiers are either derived from renewable resources such as rosin derivatives including wood rosin, tall oil, gum rosin as well as rosin esters and natural and synthetic terpenes, and derivatives of such; or are petroleum based resins such as hydrocarbon resins. Examples of useful hydrocarbon resins includes alpha-methyl styrene and other styrenic monomer based resins, branched and unbranched $C_5$ resins, $C_9$ resins, dicyclopentadiene (DCPD) based resins, as well as styrenic and hydrogenated modifications of such. Useful tackifiers typically range from being a liquid at about 25° C. (room temperature) to having a ring and ball softening point of up to about 150° C.

Preferably, the adhesive composition of the invention comprises at least one tackifier that is compatible with the polydiene block. The tackifiers are preferably rosin derivatives, particularly hydrogenated rosin based tackifiers and hydrogenated styrenated terpene resins.

Useful commercially available tackifiers include, for example, Regalite® R 91, Regalite® R R101, Regalite® R S100, Regalite® R S260, Regalrez® 1018, Regalrez® Regalrez® 3102, Regalrez® 6108, Regalrez® 5095, Zonatac® Lite series such as Zonatac® 105 Lite, Escorez® 5300 series, Foral® AX, Foral® 85 and Foral® 105.

Optionally, the adhesive composition of the invention comprises at least one plasticizer.

Preferably, for adhesive compositions that can be applied at low application temperatures, adhesive compositions exhibiting good cold temperature such as chill-grade or freezer-grade adhesives), and adhesive compositions exhibiting good adhesion to wet surfaces, the adhesive composition comprises at least one plasticizer that is compatible with polyvinyl aromatic block, known as polyvinyl aromatic block plasticizer. The vinyl aromatic block plasticizer has the function of diluting or softening the polyvinyl aromatic block in the vinyl modified block copolymer. The useful polyvinyl aromatic block plasticizers have a softening point of less than about 100° C., preferably less than about 80° C., more preferably less than about 50° C., and most preferably less than about 25° C. Also, the polyvinyl aromatic block plasticizers are typically low in molecular weight, preferably having a weight average molecular weight of less than about 3,000 g/mol, more preferably less than about 2,000 g/mol, and most preferably less than about 1,000 g/mol.

Useful commercially available polyvinyl aromatic block plasticizers include, such as Piccolastic® A5 from Hercules, which has a Ring and Ball softening point of 5° C. and a weight average molecular weight (Mw) of 430 g/mol, and Kristalex® 3070, which has a Ring and Ball softening point of 70° C. and a weight average molecular weight (Mw) of 880 g/mol from Hercules.

The amount of polyvinyl aromatic block plasticizers used in the adhesive composition of the invention is, preferably, up to 40 wt %, more preferable, from about 10 wt % to about 40 wt %, more preferably, from about 15 wt % to about 35wt %, based on the total weight of the composition.

Alternatively, or in addition to the polyvinyl aromatic block compatible plasticizer, the adhesive compositions of the invention may comprise one or more polydiene compatible plasticizers, at an amount up to about 60 wt %, preferably from about 10 wt % to about 40 wt %. The polydiene compatible plasticizers are plasticizers that are more compatible with the polydiene midblock than with the polyvinyl aromatic endblock of the vinyl modified block copolymer.

Exemplary polydiene compatible plasticizers include hydrocarbon oils, polybutene, and liquid elastomers such as liquid polyisoprene. Hydrocarbon oils are primarily those hydrocarbon oils that are low in aromatic content and are paraffinic or napthenic in character. Preferably, these oils are low in volatility, transparent and have as little color and odor as possible. The use of plasticizers in this invention also contemplates the use of olefin oligomers, low molecular weight polymers, natural oils such as vegetable oils and their derivatives and similar plasticizing liquids. Commercially available preferred polydiene plasticizers include Isolene ® 40, Isolene® 75, and Isolene® 400 from Elementis Specialty.

Depending on the intended end use, the adhesive composition of the invention may further comprise at least one second polymer in combination with the block copolymer having vinyl functionality, i.e., vinyl modified block copolymer. The second polymer may serve, in some instances, as an extender to minimize the concentration of vinyl functionality containing block copolymer to reduce the cost. In other instances, however, the second polymer is an essential ingredient that contributes synergistic adhesive properties such as improved tack in combination with high heat resistance. The second polymer is typically employed at concentrations up to about 40 wt %, preferably from about 5 wt % to about 40 wt %, and more preferably, from about 5 wt % to about 20 wt %, based on the total weight of the composition.

A wide variety of polymers may be employed as the second polymer. The second polymer is typically a second block copolymer that does not have vinyl functionality, i.e., a block copolymer that has not been 1,2-vinyl modified, a homogeneous ethylene/alpha-olefin interpolymer, an amorphous polyalphaolefin, an interpolymer of ethylene, or mixtures thereof. These polymers may be relatively insensitive to radiation curing but offer dilution or synergistic affects on adhesive properties.

A wide variety of the second block copolymers, which have not been vinyl modified, useful as a second polymer in the radiation curable adhesive composition of the invention include A-B-A triblock structures, A-B diblock structures, $(A-B)_n$ radial block copolymer structures, as well as branched and grafted versions of such, wherein the A block is a non-elastomeric polymer block, typically comprising polystyrene and/or vinyl aromatic structure and the B block is an unsaturated conjugated diene or hydrogenated version thereof. In general, the B block is typically isoprene, butadiene, ethylene/butylene, ethylene/propylene, and mixtures thereof.

Useful commercially available second block copolymers include the Kraton® D and G series block copolymers from Shell Chemical Company (Houston, Tex.), Europrene® Sol T block copolymers from EniChem (Houston, Tex.), Vector® block copolymers from Exxon (Dexco) (Houston, Tex.), as well as others.

The inventors have found that by blending at least one styrene-isoprene-styrene (SIS) block copolymer having a styrene content of less than about 25 wt % as a second block copolymer together with the vinyl modified block copolymer, the resultant adhesive composition exhibits improved tack while maintaining the high shear adhesive failure temperature (SAFT).

A homogeneous ethylene/α-olefin interpolymer is a homogenous linear or substantially linear interpolymer of ethylene and at least one $C_3$–$C_{20}$ α-olefin. The term "interpolymer" is used herein to indicate a copolymer, terpolymer, or a higher order polymer. That is, at least one other comonomer, such as, in the case of ethylene/α-olefin interpolymer, at least one $C_3$–$C_{20}$ α-olefin comonomer, is polymerized with ethylene to make the interpolymer. The term "homogeneous" means that any comonomer is randomly distributed within a given interpolymer molecule and substantially all of the interpolymer molecules have the same ethylene/comonomer ratio within that interpolymer.

The homogeneous ethylene/α-olefin interpolymer used in the preferred radiation curable adhesive compositions of the invention have a density of no greater than 0.965 g/cm$^3$, preferably no greater than 0.900 g/cm$^3$, more preferably no greater than 0.890 g/cm$^3$, and even more preferably no greater than 0.885 g/cm$^3$, and most preferably no greater than 0.880 g/cm$^3$. In the case of the radiation curable pressure sensitive adhesive compositions, the homogeneous ethylene/α-olefin interpolymers have a density of at least 0.850 g/cm$^3$, preferably at least 0.860 g/cm$^3$, and more preferably about 0.870 g/cm$^3$.

Amorphous polyalpha-olefins (APAO), also described as amorphous polyolefins, differ from homogeneous ethylene/α-olefin interpolymers, with regard to homogeneity, molecular weight distribution ($M_w/M_n$), as well as comonomer (α-olefin) content. Amorphous polyalpha-olefins are homopolymers, copolymers and terpolymers of alpha-olefins which are typically polymerized by means of processes that employ Ziegler-Natta catalysts, resulting in a relatively broad molecular weight distribution, typically greater than 4. In contrast, the homogeneous ethylene/α-olefin interpolymers are characterized as having a narrow molecular weight distribution. The homogeneous ethylene/α-olefin interpolymers have a $M_w/M_n$ of less than 4, preferably less than 3, more preferably from 1.5 to 2.5, even more preferably from 1.8 to 2.2, and most preferably about 2.0. Further, whereas amorphous polyalpha-olefins produced from Ziegler-Natta catalysis typically have an alpha-olefin concentration greater than 50 wt %, homogeneous ethylene/α-olefin interpolymers useful in the present invention are substantially ethylene, having a much greater ethylene content than α-olefin comonomer content.

Interpolymers of ethylene are polymers of ethylene and at least one comonomer selected from the group consisting of vinyl esters of a saturated carboxylic acid wherein the acid moiety has up to 4 carbon atoms, unsaturated mono- or dicarboxylic acids having 3 to 5 carbon atoms and a salt thereof, esters of the unsaturated acid derived from an alcohol having 1 to 8 carbon atoms, and mixtures thereof. Terpolymers of ethylene and these comonomers are also suitable. Particularly suitable interpolymers of ethylene are ethylene/vinyl acetate (EVA), ethylene/methyl acrylate (EMA), ethylene n-butyl acrylate (EnBA), and mixtures thereof having a relatively low comonomer content of about 25 wt % or less.

The radiation curable composition of the invention may also comprise a wax.

Particularly in the case of bottle-labeling, laminating, bookbinding, and packaging adhesives, wherein pressure sensitivity is undesirable, waxes may be usefully employed in the radiation curable adhesive compositions of the invention.

Waxes are commonly used to modify the viscosity and reduce tack at concentrations of up to about 40 wt %, and preferably from about 10 wt % to about 40 wt %, based on the total weight of the composition. Preferred waxes are those having a minimum amount of unsaturation. Paraffin wax, such as Paraffin 155F exhibits a sufficiently low amount of UV absorbing components. Other waxes may also be useful provided that the adhesive composition is cured at a temperature above the cloud point of the wax.

In general, the additional ingredients compounded with the radiation sensitive vinyl modified block copolymers typically contain low levels of unsaturation and minimal aromatic content such that the ingredients do not adversely affect the radiation responsiveness of the adhesive composition. Further, as is known in the art, various other components can be added to modify the tack, color, odor, etc., of the radiation curable adhesive composition. Additives such as antiblock additives, pigments, and fillers, can also be included in the formulations. It is generally preferred that the additives should be relatively inert and have negligible effects upon the properties contributed by the homogeneous linear or substantially linear interpolymer, tackifying agent, and plasticizer.

In the case of UV curing, one or more photoactive initiators and/or photoactive coupling agents are added to the adhesive composition. Representative examples include, but are not limited to aldehydes, benzaldehyde, acetaldehyde, and their substituted derivatives; ketones such as acetophenone, benzophenone, and their substituted derivatives, particularly the 4-alkylbenzophenones wherein the alkyl group has 1 to 18 carbon atoms; quinones such as benzoquinone, anthraquinone, and their substitutes derivatives; thioxanthones, such as 2-isopropylthioxanthone and 2-dodecylthioxanthone; and certain chromophore-substituted halomethyl-sym-triazines, such as 2,4-bis (trichloromethyl)-6-(3',4'-dimethoxyphenyl)-sym-triazine.

Another suitable type of photoinitiator that may be employed in the compositions of the present invention is the "alpha cleavage type" photoinitiator. This photoinitiator is particularly beneficial when other unsaturated species such as acrylated oligomers and monomers are further employed. Alpha cleavage type photoinitiators are known in the art. Commercial examples include Irgacure 184 and Darocur 1173, both available from Ciba-Giegy (Hawthorne, N.Y.).

Preferred radical type photoinitiators include acylphosphine oxides, bisacrylphosphine oxides, and mixtures thereof, and blends in which they are included. Useful commercially available examples include Irgacure® 819, Irgacure® 1800, and Irgacure® 1850 from Ciba; and Lucirin TPO from BASF.

Photoactive initiators and photoinduced coupling agents are present at a concentration of from about 0.05 wt % to about 3 wt %, preferably from about 0.1 wt % to about 2.0 wt % and more preferably from about 0.3 wt % to about 1.5 wt %, based on the total weight of the composition for UV curable compositions. However, in the case of electron-beam (EB) radiation curing, photoactive agents are not needed to crosslink the block copolymer having vinyl functionality.

To cure the composition of the invention, a source of actinic radiation of sufficient energy (i.e., wavelength ranges) to generate free radicals when incident upon the particular photoinitiator selected for use in composition should be chosen. The preferred wavelength ranges for the photoinitiators disclosed above is 400 to 250 nm.

The amount of radiant energy density desired to crosslink the adhesive film or coating formed from the composition of the invention is from about 25 to about 200 mJ/cm$^2$, (for UVA, from about 315 nm to about 400 nm), more preferably from about 40 to about 200 mJ/cm$^2$, (for UVA, from about 315 nm to about 400 nm), as measured with a Power-Puck™ radiometer manufactured by EIT. Details of the photocure process are disclosed in U.S. Pat. Nos. 4,181,752 and 4,329,384, incorporated herein by reference.

The compositions of the invention can also be cured by means of electron-beam (EB) radiation without using photoinitiators. The dosage needed to crosslink the compositions vary depending on the particular composition but generally ranges from about 1 to about 20 Mrads, preferably from about 2 to about 10 Mrads. Details of suitable processes for electron-beam (EB) curing of adhesives-coated substrates can be found in U.S. Pat. No. 4,533,566, which is incorporated herein by reference.

The radiant energy density and thus, the line speed for sufficient curing is dependent on the composition and more importantly the thickness of the adhesive film being cured. For about 1 mil adhesive films, the adhesive compositions are sufficiently cured at line speeds ranging from about 300 ft/min to about 500 ft/min when curing with 2×600 w lamps.

Depending on the kinds and amounts of ingredients that are combined with the block copolymer having vinyl functionality, the resultant adhesive composition exhibits at least one of a variety of improved properties. In some embodiments, the adhesive composition advantageously has the Brookfield viscosity of less than about 10,000 cps at about 160° C., preferably less than about 8,000 cps at about 160° C., more preferably less than about 6,000 cps at about 160° C., and even more preferably, less than about 4,000 cps at about 160° C., that allows the adhesive composition applied at a low application temperature, i.e., an application temperature of no greater than about 150° C., preferably, no greater than about 140° C. and more preferably, no greater than about 130° C. The adhesive composition applied at low application temperature may be characteristically described as a "warm melt" adhesive since the composition exhibits a low viscosity at even lower temperatures. Hence, the composition exhibits the desired viscosity at a temperature of less than about 140° C., and preferably at a temperature of less than about 130° C. In the most preferred embodiments, the adhesive composition is sufficiently fluid at about 120° C. The low application temperature is amenable to coating to heat sensitive substrates, such as low gauge polyethylene film. The low application temperature also aids in preventing thermal degradation of the adhesive composition.

The adhesive compositions of the invention can be formulated such that the compositions exhibit improved plasticizer resistance, sufficient tack and improved heat resistance. Preferably, the shear adhesion failure temperature (SAFT) is no less than about 300° F., and more preferably, no less than about 350° F., and the static shear is no less than about 24 hours after curing of the adhesive composition. In the case of pressure sensitive adhesives, the high heat resistance as indicated by high SAFT is coupled with sufficient tack, depending on the end use intended. The Loop Tack is typically at least about 30 oz/in (1.875 lb/in), preferably about 50 oz/in (3.125 lb/in) or greater, and more preferably, about 75 oz/in (4.6 lb/in) or greater. For permanent grade pressure sensitive adhesives, the 180° Peel value is typically at least about 2.5 lbs/linear inch (pli), preferably at least about 3.0 lbs/linear inch (pli), and more preferably at least about 4 lbs/linear inch (pli) or greater depending of the intended end use.

The adhesive composition exhibits good plasticizer resistance and solvent resistance. The plasticizer resistance is particularly advantageous for bonding highly plasticizer substrates such as various oil extended elastomers based substrates. The compositions are also resistant to exposure to oil based skin care products that may be incorporated in disposable absorbent products.

The adhesive may be bonded to a variety of substrates such as various films, nonwovens, paperstock, paperboard, plastics, metals, painted substrates, glass, leather, rubber, etc.

The adhesive compositions of the invention can be used for various applications including for use as pressure sensitive adhesives for high performance tapes and labels, and particularly for automotive applications such as window labels and license plate tabs, sterilizable medical applications, freezer-grade labels, shrinkable label for contoured containers, hook and loop tapes, abrasive products, road marking tapes, foam bonding, bonding rubber gaskets to air filters and positioning adhesives. Further, both pressure sensitive as well as non-pressure sensitive adhesive compositions can be employed for film laminating and nonwoven construction applications such as disposable diaper construction as well as for wood flooring adhesives. Further, the adhesive compositions are low in odor.

In another aspect, the invention is directed to a double-faced tape and a method of producing the same. The double-faced tape is formed from a single layer of the adhesive composition of the invention. It comprises a first surface and a second opposing surface without having any supporting substrate in between the two surfaces. Upon radiation cure the first surface exhibits a first 180° peel value and a second opposing surface exhibits a second 180° peel value that is greater than the first peel value. Preferably, the ratio of the second peel value to the first peel value is from about 2:1 to about 20:1, more preferably, from about 4:1 to about 20:1.

According to the invention, the double-faced tape is prepared by applying a radiation curable adhesive composition of the invention onto a release-coated surface to obtain an adhesive film having a first surface and a second opposing surface that is disposed on the release-coated surface; and curing said adhesive film by exposing the first surface of it to radiant energy to obtain a double-faced tape, of which the two surfaces exhibit differential adhesion. It is believed, but not bound by any theory, that curing the adhesive film to a different extent on the first surface of the adhesive layer in comparison to the second opposing surface of the same adhesive layer creates the differential adhesion. The differential adhesion properties obtained depend on the thickness of the adhesive layer, radiation cure conditions such as line speed and lamp output.

The thickness of the adhesive film is typically at least about 3 mils and preferably, from about 4 to 10 mils. The adhesive composition is compounded in such a manner that the radiant energy, such as the light in the case of UV cure, does not uniformly penetrate the adhesive film through the entire thickness. Thus, the adhesive surface closer to the radiant energy source tends to crosslink to a much greater extent than the opposing surface of the adhesive film further from the radiant energy source. Upon cure by means of radiation, the first surface of the adhesive film exhibits removable-grade adhesive characteristics and the second opposing surface exhibits permanent-grade adhesive characteristics. The peel value of the permanent-grade adhesive surface is typically at least two times that of the opposing adhesive surface and preferably 4 to 20 times greater.

The applicants have also discovered that the compositions of the invention, particularly the compositions comprising at least one polyvinyl aromatic block plasticizer exhibit excellent adhesion to wet surfaces in addition to maintaining good adhesion properties throughout a temperature range from about 0° C. to about 100° C. Such properties are amenable to be utilized in a plastic wrap product comprising a film layer and a releasably sealable adhesive such as set forth in U.S. Pat. No. 5,662,758, incorporated herein by reference. Good adhesion to wet surfaces and stable adhesive properties without transfer are also important characteristics for medical grade adhesives that are bonded to skin.

The invention is further illustrated by the following non-limiting examples. It should be understood, however, that many variations and modifications may be made while remaining within the scope of the present invention. All the ingredients are in percentage by weight unless otherwise stated. The shear adhesion failure temperatures (SAFT) were tested according to the SAFT Testing Method I unless otherwise stated.

EXAMPLE

Test Methods
Brookfield Viscosity

Brookfield viscosity is measured with a Brookfield RVDT Viscometer in accordance with the manufacturer's operating instructions.

Peel Testing

Peel value is measured in accordance with PSTC-1, revised 8/85, "Peel Adhesion of Single Coated Pressure-Sensitive Tapes at 180° Angle". The adhesive is coated at a temperature of 350° F. (177° C.) onto 2 mil Mylar™ (polyethylene terephthalate) at the coating thickness of 1 mil. The coated Mylar™ is cut into strips of 1 inch in width by 6 inches in length (2.5 cm by 15.2 cm). The strips is then adhered to stainless steel plates, reporting the average peel value of four (4) samples at room temperature (25° C.).

Static Shear

Static shear is measure in accordance with PSTC-7, revised 8/85, "Holding Power of Pressure Sensitive Tapes". 1"×1" samples are coated in the same manner as described in the Peel Testing. The samples are laminated onto a stainless steel test panel with a 4.5 pound (2.0 kg) hand roller and allowed to dwell for 20 minutes prior to testing. A 500 g load is employed, reporting the average static shear of four (4) samples and the failure mode at temperature indicated.

Loop Tack

Loop tack is measured in accordance with FINAT Test Method No. 9 (FTM 9)

The samples are coated in the same manner as described in the Peel Testing. The samples are adhered to stainless steel at room temperature, reporting the average loop tack value of five (5) samples and the failure mode.

Rheology Testing

The storage modulus (G') and tan delta are determined in accordance with ASTM D4440-93. A test frequency of 10 radians/sec and a temperature ramp or step test is performed with a 10 mm diameter parallel plate test geometry with a gap of 1 to 4 mm.

Shear Adhesion Failure Temperature (SAFT) Test Method I

The 1"×1" adhesive film on 2 mil Mylar™ (polyethylene terephthalate) substrate is placed on a solvent cleaned stainless steel panel and rolled down with a standard 4.5 lb roller. The sample sat for 30 minutes at 73° F./50% relative humidity and then, is placed in a 200° F oven. A 500 gram weight is suspended from each sample. After one minute equilibration, the timer is started and the oven temperature is increased at a rate of 1° F. per minute to a final temperature of 350° F., reporting the average failure temperature of four (4) samples.

Shear Adhesion Failure Temperature (SAFT) Test Method II

A first 12" long sheet of Mylar™ is taped to a heavy chip board. Two pieces of release paper are taped onto the Mylar™ parallel to each other, one inch apart. A second 12" long sheet of Mylar™ is taped on top of the first Mylar™ containing release paper. The second Mylar™ sheet is folded backward. Sandwich the second sheet of Mylar™ between two glass rods, having the front glass rod equipped with two pieces of masking tape wrapped around it. This will achieve a desired film thickness of adhesive when the adhesive is spread with the glass rod. A puddle of adhesive is poured onto the first sheet of Mylar™ between two release paper. The glass rods are pulled to spread the adhesive in a consistent film and mate the second sheet of Mylar™ to the first sheet thus forming a bond. The resultant bond is about 1"×12". This is then cut into 12 pieces as samples, each containing a 1"×1" bonded area. The samples are conditioned in an oven at 130° F. for approximately 5 minutes and then exposed to UV radiation. Intensity of radiation is recorded. The samples are turned over and the conditioning and UV radiation are repeated to ensure adequate curing through the adhesive film. The samples are then placed in an oven with a 500 gram weight applied in shear mode. The oven temperature increases at 25° C./hour. The temperature at which failure occurred is recorded, reporting the average failure temperature of four (4) samples.

Peel Adhesion Failure Temperature (PAFT)

A first 12" long sheet of Mylar™ is taped to a heavy chip board. Two pieces of release paper are taped onto the Mylar™ parallel to each other, one inch apart. A second 12" long sheet of Mylar™ is taped on top of the first Mylar™ containing release paper. The second Mylar™ sheet is folded backward. Sandwich the second sheet of Mylar™ between two glass rods, having the front glass rod equipped with two pieces of masking tape wrapped around it. This will achieve a desired film thickness of adhesive when the adhesive is spread with the glass rod. A puddle of adhesive is poured onto the first sheet of Mylar™ between two release paper. The glass rods are pulled to spread the adhesive in a consistent film and mate the second sheet of Mylar™ to the first sheet thus forming a bond. The resultant bond is about 1"×12". This is then cut into 12 pieces as samples, each containing a 1"×1" bonded area. The samples are conditioned in an oven at 130° F. for approximately 5 minutes and then exposed to UV radiation. Intensity of radiation is recorded. The samples are turned over and the conditioning and UV radiation are repeated to ensure adequate curing through the adhesive film. The samples are then placed in an oven with a 100 gram weight applied in peel mode. The oven temperature increased at 25° C./hour. The temperature at which failure occurred is recorded, reporting the average failure temperature of four (4) samples.

EXAMPLES

The ingredients employed in the examples are listed in the following Table A

TABLE A

| Tradename | Chemical Description | Supplier |
|---|---|---|
| Kraton D KX-222CS | 18% styrene $SB_2B_2$, 53%–63% vinyl butadiene | Shell |
| SR-8272 | 22% styrene, 10% vinyl butadiene, 12 MI Linear multiblock S-B-S block copolymer | Firestone |
| SR-8273 | 22% styrene, 47% vinyl butadiene, 12 MI Linear multiblock S-B-S block copolymer | Firestone |

TABLE A-continued

| Tradename | Chemical Description | Supplier |
|---|---|---|
| Piccolastic A-5 | 5° C. styrenic monomer based endblock plasticizer | Hercules |
| Kaydol Oil | white mineral oil midblock plasticizer | Witco |
| ECR-149-B | 85° C. hydrogenated aromatic midblock resin | Exxon |
| Regalrez 1094 | 94° C. hydrogenated aromatic midblock resin | Hercules |
| Regalrez 1018 | 94° C. hydrogenated aromatic midblock resin | Hercules |
| Foral AX | 68° C. hydrogenated rosin acid tackifying resin | Hercules |
| Zonatac 105 | 105° C. hydrogenated styrenated terpene resin | Arizona |
| Septon 2043 | 13% styrene, 14 MFR (200° C./10 kg) SEPS | Kurraray |
| Kraton G-1657 | 13% styrene, 35% diblock, 8 MI S-EB-S | Shell |
| Kraton G-1780 | 6% styrene S-EB-S block copolymer | Shell |
| Kraton G-1651 | 33% styrene, 100% triblock S-EB-S block copolymer | Shell |
| Kraton G-1650 | 29% styrene, 100% triblock S-EB-S block copolymer | Shell |
| Kraton G-1726 | 30% styrene, 70% diblock, 65 MI SEBS | Shell |
| Kraton D-1119 | 22% styrene, 65% diblock SIS | Shell |
| Kraton D-1111 | 22% styrene, 3 MI Linear SIS | Shell |
| Rextac 2715 | 1500 mpas 110° C. butene-1 copolymer | Rexene |
| Affinity SM-8400 | .870 g/cm$^3$, 30 MI EO homogeneous interpolymer | Dow |
| .870 g/cm$^3$/1000 MI | ethylene-octene homogeneous interpolymer | Dow |
| .858 g/cm$^3$/30 MI | ethylene-octene homogeneous interpolymer | Dow |
| Irganox 1010 | hindered phenolic antioxidant | CibaGiegy |
| Irganox 3052 FF | 2-propanionc acid radical scavenger | CibaGiegy |
| Irgafos 168 | phosphite cosynergist antioxidant | CibaGiegy |
| Irgacure 819 | photoinitiator | CibaGiegy |
| Irgacure 651 | photinitiator | CibaGiegy |
| Isolene 40-S | 40,000 Mw, 360–550 poise at 38° C. polyisoprene | Elementis |
| Sumilizer GS | 2-[1-(2-hydroxy-3,5-di-tert-pentylphenyl) ethyl]-4,6-di-tert pentylphenyl acrylate antioxidant | Sumitomo |
| Sumilizer TP-D | pentraerythrityl tetrakis-(3-dodecylthiopropionate) antioxidant | Sumitomo |
| Sylvalac ZT 105 LT | styrenated terpene tackifier | Arizona |
| Regalite R-101 | 100° C. hydrogenated aromatic midblock resin | Hercules |
| Kristalex 3070 | 70° C. pure monomer endblock placticizer | Hercules |
| WAX Paraffin 155° F. | 155° F. melt point paraffin wax | Bareco |

Examples 1–5

Adhesive compositions were prepared by combining the ingredients according to Table I. In addition to the listed ingredients, the compositions also contained 0.3 wt % each of Irganox 1010, Irganox 3052 FF and Irgafos 168 antioxidants and 0.8 wt % of Irgacure 819 photoinitiator, except for the composition of Example 3 that contained 0.4 Sumilizer GS and 0.5 Sumilizer TP-D as alternative antioxidants. The Brookfield viscosities of the compositions were tested and the data are listed in Table II.

A 1 mil coating of the composition of Example 1 was applied onto a Mylar™ (polyethylene terephthalate) film, then cured by exposure to 7.5 Mrad of electronic beam (EB).

The 180° Peel value tested before cure and after cure showed an increase of from 0.9 lbs/in (pre-cure) to 1.2 lbs/in (after cure). The radiation induced crosslinking eliminated the cohesive failure tendencies.

The adhesive compositions of Examples 2–5 were applied to Mylar™ (polyethylene terephthalate) films and cured by exposing to a 600 watt H bulb lamp at 50 feet per minute. SAFT, 180 peel values and loop tack were tested and the data are listed in Table III.

TABLE I

|  | Ex. 1 | Ex. 2 | Ex. 3 | Ex. 4 | Ex. 5 |
|---|---|---|---|---|---|
| KX-222CS | 12.0 | 19.8 | 19.8 | 19.7 | 24.6 |
| Piccolastic A-5 | 12.0 | 19.5 | — | 19.7 | 9.8 |
| Kristalex 3070 | — | — | 19.5 | — | — |
| Regalrez 1018 | 74.4 | 36.9 | 36.9 | 58.9 | 54.1 |

TABLE I-continued

|  | Ex. 1 | Ex. 2 | Ex. 3 | Ex. 4 | Ex. 5 |
|---|---|---|---|---|---|
| Foral AX | — | 22.1 | — | — | 9.8 |
| ECR-149B | — | — | 22.1 | — | — |

TABLE II

| Brookfield viscosity (cps) | | | | | |
|---|---|---|---|---|---|
|  | Ex. 1 | Ex. 2 | Ex. 3 | Ex. 4 | Ex. 5 |
| Visc. at 160° C. | 385 | 1,950 | 3,850 | 640 | 4,200 |
| Visc. at 300° F. |  |  | 5,400 |  |  |
| Visc. at 250° F. | 2165 |  | 18,800 |  |  |
| Visc. at 200° F. | 4120 | 22,000* | 112,000 |  |  |

*Visc. at 100° C.

TABLE III

| Adhesive Properties | | | | |
|---|---|---|---|---|
|  | Ex. 2 | Ex. 3 | Ex. 4 | Ex. 5 |
| 180° Peel (lbs/in) | 2.5 | — | 0.8 | 1.1 |
| Loop Tack (lb/in) | 6.25 | 2.5 | 3.6 | 1.2 |
| SAFT (° F.) | >350 | >350 | >350 | >350 |
| Static Shear (at 100° C.) | >24 hours | — | — | — |

Examples 1–5 represent low application temperature pressure sensitive adhesives that can advantageously be applied as low as 200° F. Example 2 also advantageously has very high initial tack. In addition, the composition of example 2 was also tested for adhesion on Pyrex glass substrate. The 180° peel values on dry and wet Pyrex glass substrates were 3.9 lb/in and 1.2 lb/in, respectively, at a coat weight of 12.5 grams, according to the Peel Testing Method with the exception of using a Pyrex glass plate instead of a stainless steel plate. It is shown that the composition exhibits high peel value to low energy surfaces, particularly wet surfaces, Example 6

An adhesive composition is prepared by combining 30 parts KX-222C, 52.9 parts ECR-149-B, 14.2 parts Kaydol Oil, 1 part Sumilizer GS, 1 part Sumilizer TPD and 0.9 parts Irgarcure 819. The Brookfield viscosity, 180° peel value, loop tack, SAFT and static shear of the composition was tested and the data are listed in Table IV.

A 10 mil thick adhesive film of the composition was coated onto release paper and cured at 60 feet per minute (fpm) by exposing to a 600 watt H bulb lamp from Fusion to obtain a double-faced tape. The 180° peel values on both surfaces of the double-faced tape were tested and the data is listed in Table V.

TABLE IV

| Brookfield Viscosity (cps) | |
| --- | --- |
| at 275° F. | 63,000 |
| at 300° F. | 33,063 |
| at 325° F. | 18,750 |
| at 350° F. | 11,600 |
| 180° Peel | 4.0 lbs/in |
| Loop Tack | 30 oz/in |
| SAFT | >350° F. |
| Static Shear (at 100° C.) | >24 hours |

Example 7

An adhesive composition was prepared according to Example 6, except using SR-8273 instead of KX-222C and 1.9 parts Irgarcure 819 instead of 0.9 parts Irgarcure 819.

The samples were coated onto release paper at 4.0 mils adhesive thickness and then cured at 100 and 300 feet per minute (fpm), respectively, by exposing to a 600 watt H bulb lamp. The 180° peel values on both surfaces of the double-faced tape samples were tested and the data is listed in Table V.

TABLE V

| | 180° Peel Values of the Double-faced Tape | | |
| --- | --- | --- | --- |
| | Ex. 6 | Ex. 7-A (cured at 100 fpm) | Ex. 7-B (cured at 300 fpm) |
| First Surface | 0.1 pli, 100% AF | 1.565 pli | 1.840 pli |
| Second Surface | 7.54 pli, 100% AF | 5.824 pli | 6.334 pli |

As shown in Table V, the double-faced tape of the invention exhibited different adhesion levels on opposing surfaces of the adhesive film due to differential curing of the adhesive film formed from the single composition. The adhesive composition is particularly useful for the tape market to create a transfer tape having differential adhesion employing a single adhesive composition in the absence of a backing. Traditionally, a double-faced tape is made by coating a permanent grade adhesive on one surface of a Mylar™ backing film and a removable grade adhesive on the opposite surface of the backing film.

Examples 8–19

Adhesive compositions were prepared by combining the ingredients according to Table VII and Table VIII. SAFT, 180 peel values and loop tack were tested and the data are listed in Table IX.

Examples 8–10 demonstrate that random multiblock styrene-butadiene-styrene (SBS) block copolymers having either low vinyl or high vinyl functionality are radiation curable. Examples 11–16 exemplify adhesive compositions having improved heat resistance. These examples also demonstrate that blends of the vinyl functionalized block copolymer in combination with homogeneous ethylene/alpha-olefin interpolymers resulted in the highest SAFT values in combination with improved peel and loop tacks. Examples 18 and 19 relative to Example 17 demonstrates that blends of the vinyl functionalized block copolymer in combination with styrene-isoprene-styrene (SIS) increases the peel and loop tack without compromising the heat resistance.

TABLE VII

| | Ex. 8 | Ex. 9 | Ex. 10 | Ex. 11 | Ex. 12 | Ex. 13 |
| --- | --- | --- | --- | --- | --- | --- |
| KX-222C | 30 | | | 20 | 20 | 20 |
| SR-8273 | | 30 | | | | |
| SR-8272 | | | 30 | | | |
| Affinity SM-8400 .870 g/cm³/1000 MI | | | | 10 | 10 | |
| Rextac 2715 | | | | | | 10 |
| Zonatac 105 | 52.9 | 52.9 | 52.9 | 52.9 | 52.9 | 52.9 |
| Kaydol Oil | 14.2 | 14.2 | 14.2 | 14.2 | 14.2 | 14.2 |
| Sumilizer GS | 1 | 1 | 1 | 1 | 1 | 1 |
| Sumulizer TP-D | 1 | 1 | 1 | 1 | 1 | 1 |
| Irgacure 819 | 0.9 | 0.9 | 0.9 | 0.9 | 0.9 | 0.9 |

TABLE VIII

| | Ex. 14 | Ex. 15 | Ex. 16 | Ex. 17 | Ex. 18 | Ex. 19 |
| --- | --- | --- | --- | --- | --- | --- |
| KX-222C | 20 | 20 | 20 | 40 | 20 | 20 |
| Kraton G-1780 | 5 | | | | | |
| Kraton G-1650 | | 5 | | | | |
| Kraton G-1726 | | | 10 | | | |
| Kraton D-1119 | | | | | 20 | |
| Kraton D-1111 | | | | | | 20 |
| Zonatac 105 | 55.4 | 55.4 | 52.9 | 47.9 | 47.9 | 47.9 |
| Kaydol Oil | 16.7 | 16.7 | 14.2 | 9.2 | 9.2 | 9.2 |
| Sumulizer GS | 1 | 1 | 1 | 1 | 1 | 1 |
| Sumulizer TP-D | 1 | 1 | 1 | 1 | 1 | 1 |
| Irgacure 819 | 0.9 | 0.9 | 0.9 | 0.9 | 0.9 | 0.9 |

TABLE IX

| Ex. No. | SAFT (° F.) (uncured) | SAFT (° F.) (cured) | 180° Peel Value (pli) | Loop Tack (lbs./in²) |
| --- | --- | --- | --- | --- |
| Ex. 8 | 174 | >350 | 4.1, 100% AF* | 1.25 |
| Ex. 9 | 141.5 | >350 | 3.1, 90% AF*, | |
| Ex. 10 | 126 | >335–350 | 3.5, 100% AF* | |
| Ex. 11 | 147.5 | >350 | 5.4, 100% AF* | 4.0 |
| Ex. 12 | 138 | >350 | 5.0, 100% AF* | 1.9 |
| Ex. 13 | 132.5 | 186 | 5.7, 30% CF* | 1.7 |
| Ex. 14 | 151 | >350 | 4.5 100% AF* | |
| Ex. 15 | 162 | >350 | 4.5, 100% AF* | 2.1 |
| Ex. 16 | 162 | 330 | 4.3 | 1.8 |
| Ex. 17 | 201 | 350 | 3.4, 100% AF* | 2.8 |

TABLE IX-continued

| Ex. No. | SAFT (° F.) (uncured) | SAFT (° F.) (cured) | 180° Peel Value (pli) | Loop Tack (lbs./in²) |
|---------|---|---|---|---|
| Ex. 18 | 188 | 350 | 3.6, 100% AF* | 2.6 |
| Ex. 19 | 193 | >350 | 5.0, 100% AF* | 4.2 |

AF*: adhesive failure, i.e., the adhesive remains on the Mylar ™ substrate.
CF*: cohesive failure, i.e., failure due to separation within the adhesive layer, resulting in a significant amount of adhesive left on the Mylar ™ substrate and the stainless steel test panel.

Example 20

An adhesive composition was prepared by combining the ingredients according to Table X. A 10 mil thick adhesive film of the composition was coated onto a loop substrate and cured at 60 feet per minute (fpm) by exposing to a 600 watt H bulb lamp from Fusion. 180° peel value, SAFT, loop tack and static shear were tested and the data is listed in Table X.

TABLE X

| KIX-222C | 21.2 |
| ECR-149-B | 51.3 |
| Kaydol Oil | 5.0 |
| Isolene 40-S | 20 |
| Sumilizer GS | 1.0 |
| Sumilizer TP-D | 1.0 |
| Irgacure 819 | 0.5 |
| Adhesive Properties | |
| 180° Peel (lbs/in) | 4.4 |
| Loop Tack (oz/in) | 45 |
| SAFT (° F.) | >350 |
| Static Shear (at 100° C.) (hr) | >24 |

Example 21

An adhesive composition was prepared by combining the ingredients according to Table XI. The composition obtained had an initial Brookfield viscosity of 380 cps at 300° F. and 385 cps at 325° F. Thermostability was confirmed by monitoring viscosity at application temperature of 325° F. over 24 hours. The viscosity remained 385 cps.

TABLE XI

| KX-222CS | 15 |
| Irganox 1010 | 0.23 |
| Irganox 3052 FF | 0.23 |
| Irgafos 168 | 0.23 |
| Regalrez 1018 | 27.7 |
| ECR-149B | 16.5 |
| Piccolastic A5 | 15.0 |
| Paraffin 155F | 24.6 |
| Irgacure 819 | 0.6 |

The adhesive composition was coated onto a Mylar™ film at about 1.0–1.5 mil thickness and cured with a 600 W/inch H bulb at 70 feet per minute. SAFT tested on the 1"×1" overlap adhesive to Mylar™ was greater than 350° F.

The adhesive composition was also coated onto a standard coated 3"×9" paper label stock at about 1.0–1.5 mil and the performance was evaluated and reported as follows:

| | Before Cure | After Cure |
|---|---|---|
| Pick-up bond evaluation to glass | Fiber Tear | Fiber Tear |
| Overlap bond evaluation | Fiber Tear | Fiber Tear |

The adhesive composition was also coated onto an oriented polypropylene (OPP) 2 mil film label at about 1.0 mil, then, bonded to the front side of a second piece of label stock and cured through the clear overlap at 100 fpm with a 600 W/inch H bulb. This simulates the overlap portion of a typical roll-fed label. SAFT tested on the 1"×1" overlap adhesive to OPP was about 190° F. Overlap bond evaluation showed strong substrate deformation.

As shown by the above properties, the adhesive composition is a low viscosity hot-melt adhesive designed for adhering labels to containers such as plastic and glass containers. The high SAFT value confirms the excellent performance under stress and heat necessary to allow the filmic label to shrink under exposure to heat keeping the seam tight. In this way the label can conform to the size and shape of the container. The cured adhesive exhibiting high heat resistance is recommended for shrink-labeling.

Examples 22–24

Adhesive compositions of Examples 22–24 were prepared by combining the ingredients according to the following Table XII. The compositions were then tested according to the PAFT Testing Method and the SAFT Testing Method II. The data is listed in Table XIII.

TABLE XII

| Ingredients | Ex. 22 | Ex. 23 | Ex. 24 |
|---|---|---|---|
| KX-222C | 21 | 28 | 31 |
| Isolene 40 | 15 | 8 | 5 |
| P. Wax 155 | 25 | 25 | 25 |
| Zonatack 105 LT | 37.37 | 37.16 | 37.07 |
| Sumilizer GS | 0.5 | 0.5 | 0.5 |
| Sumilizer TP-D | 0.5 | 0.5 | 0.5 |
| Irgacure 819 | 0.63 | 0.84 | 0.93 |

TABLE XIII

| Ex. No. | Brookfield Viscosity (cps) | Film thickness (mil) | PAFT (° F.) | SAFT (° F.) |
|---|---|---|---|---|
| 22 | 6280 (300° F.) | 7 | 132 | >350 |
|    | 2100 (350° F.) | 11 | 135 | 275[3] |
| 23 | 5450 (350° F.) | 10–13 | 128[1] | 339[4] |
| 24 | 9360 (350° F.) | 13–18 | 127[2] | 304[5] |

[1]Average of 9 samples;
[2]Average of 8 samples;
[3]Average of 5 samples;
[4]Average of 10 samples;
[5]Average of 7 samples.

Examples 22–24 represent non-pressure sensitive adhesive compositions that are useful for casemaking application as a replacement for animal glue. The compositions are also useful for other bookbinding applications, particularly one-shot bookbinding, as well as various packaging applications. The compositions maintain sufficient tack after exposure to UV light to mate the adhesives to book cover materials and obtain good adhesion. The tack is lost as the adhesive sets. The adhesives have outstanding SAFT with moderate PAFT. They also have excellent flexibility. This flexibility would provide good layflat characteristics that are important in one-shot bookbinding.

What is claimed are:

1. A radiation curable hot melt adhesive composition comprising:
   a) from about 10% by weight to about 40% by weight of at least one block copolymer having at least two blocks, wherein the first block is a polyvinyl aromatic block and the second block is a polydiene block having vinyl functionality;
   b) from about 0% by weight to about 20% by weight of a second polymer; and
   c) from about 10% by weight to about 90% by weight of at least one tackifier;
   said adhesive composition having a viscosity of less than 6,000 cps at a temperature of 160° C.

2. The adhesive composition of claim 1, wherein said adhesive composition crosslinks through said vinyl functionality upon exposure to radiant energy.

3. The adhesive composition of claim 1, wherein the total content of the block copolymer and the second polymer is at least 15% by weight based on the total weight of the composition.

4. The adhesive composition of claim 1, wherein said tackifier is a polydiene compatible tackifier.

5. The adhesive composition of claim 4, further comprising a polyvinyl aromatic block compatible plasticizer.

6. The adhesive composition of claim 1, wherein from about 30% by weight to about 90% by weight of the ingredients of the composition is liquid at ambient temperature.

7. The adhesive composition of claim 5, wherein from about 30% by weight to about 90% by weight of the ingredients of the composition is liquid at ambient temperature.

8. The adhesive composition of claim 1, wherein said adhesive composition exhibits a loop tack of greater than 3 lb/in and a shear adhesion failure temperature of at least 300° F.

9. The adhesive composition of claim 8, wherein said adhesive composition exhibits a loop tack of greater than 4.6 lb/in.

10. The adhesive composition of claim 1, wherein said adhesive composition has a viscosity of less than 6,000 cps at a temperature of 140° C.

11. A radiation curable hot melt adhesive composition comprising:
    a) from about 10% by weight to about 40% by weight of at least one block copolymer having at least two blocks wherein the first block is a polyvinyl aromatic block and the second block is a polydiene block having vinyl functionality;
    b) from about 10% by weight to about 80% by weight of at least one tackifier that is compatible with the polydiene block; and
    c) from about 10% by weight to about 40% by weight of at least one plasticizer selected from the group consisting of polyvinyl aromatic block compatible plasticizers having softening point of no greater than 100° C., polydiene compatible plasticizers having a weight average molecular weight of no less than 20,000, and the combinations thereof.

12. The adhesive composition of claim 11, wherein said polyvinyl aromatic block compatible plasticizers have a softening point of less than about 80° C.

13. The adhesive composition of claim 11, wherein said polyvinyl aromatic block compatible plasticizers have a softening point of less than about 50° C.

14. The adhesive composition of claim 11, wherein said polyvinyl aromatic block compatible plasticizers have a softening point of less than about 25° C.

15. The adhesive composition of claim 11, wherein said polydiene compatible plasticizers having a weight average molecular weight of from about 20,000 to about 100,000.

16. A radiation curable hot melt adhesive composition comprising:
    a) from about 10% by weight to about 40% by weight block copolymer having at least two blocks wherein the first block is a polyvinyl aromatic block and the second block is a polydiene block having vinyl functionality, said second block having a vinyl content of from 25 to 70% by weight;
    b) from about 5% by weight to about 40% by weight of at least one second polymer selected from the group consisting of styrenic block copolymers, ethylene/$\alpha$-olefin interpolymers, interpolymers of ethylene, and mixtures thereof; and
    c) from about 10% by weight to about 90% by weight of at least one tackifier.

17. The adhesive composition of claim 16, wherein said styrenic block copolymer is selected from the group consisting of styrene-ethylene/butylene-styrene, styrene-isoprene-styrene, styrene-ethylene/butylene, styrene-ethylene/propylene, and mixtures thereof.

18. The adhesive composition of claim 16, wherein said styrenic block copolymer is a styrene-isoprene-styrene block copolymer having a styrene content of less than about 25% by weight.

19. The adhesive composition of claim 16, wherein said second polymer consists of homogeneous linear or substantially linear ethylene/$\alpha$-olefin interpolymers of ethylene and at least one $C_3$ to $C_{20}$ $\alpha$-olefin.

20. The adhesive of claim 19, wherein said ethylene/$\alpha$-olefin interpolymers have a density of less than about 0.885 g/cm$^3$.

21. A radiation curable hot melt adhesive composition comprising:
    a) from about 10% by weight to about 50% by weight of at least one block copolymer having at least two blocks wherein the first block is a polyvinyl aromatic block and the second block is a polydiene block having vinyl functionality, said second block having a vinyl content of from about 25% by weight to 70% by weight;
    b) from about 20% by weight to about 55% by weight of at least one tackifier;
    c) from about 10% by weight to about 40% by weight of at least one wax; and
    d) from about 0% by weight to about 35% by weight of at least one plasticizer.

22. The adhesive composition of claim 21, wherein said adhesive composition is substantially nontacky at a temperature lower than the cloud point of said wax.

23. The adhesive composition of claim 21, wherein said adhesive composition is cured at a temperature above the cloud point of said wax.

24. A label comprising:
    a substrate, and
    the adhesive composition of claim 21, disposed on said substrate.

25. The label of claim 24, wherein said label shrinks upon exposure to heat.

26. A radiation curable adhesive composition comprising:
a) from about 10% by weight to about 40% by weight of at least one block copolymer having at least two blocks wherein the first block is a polyvinyl aromatic block and the second block is a polydiene block having vinyl functionality;
b) from about 5% by weight to about 40% by weight of at least one homogeneous linear or substantially linear ethylene/α-olefin interpolymer of ethylene and at least one $C_3$ to $C_{20}$ α-olefin, said ethylene/α-olefin interpolymer having a density of less than about 0.885 $g/cm^3$; and
c) from about 10% by weight to about 90% by weight of at least one tackifier.

27. A radiation curable adhesive composition comprising:
a) from about 10% by weight to about 50% by weight of at least one vinyl modified block copolymer having at least two blocks wherein the first block is a polyvinyl aromatic block and the second block is a polydiene block having vinyl functionality;
b) from about 20% by weight to about 55% by weight of at least one tackifier;
c) from about 10% by weight to about 40% by weight of at least one wax; and
d) from about 0% by weight to about 35% by weight of at least one plasticizer;
wherein said adhesive composition cures at a temperature above the cloud point of said wax.

28. The adhesive composition of claim 16, wherein said second block has a vinyl content of from about 45% by weight to about 75% by weight.

29. The adhesive composition of claim 21, wherein said second block has a vinyl content of from about 45% by weight to 75% by weight.

30. A radiation curable hot melt adhesive composition comprising:
a) from about 10% by weight to about 40% by weight block copolymer having at least two blocks wherein the first block is a polyvinyl aromatic block and the second block is a polydiene block having vinyl functionality;
b) from about 5% by weight to about 40% by weight of at least one second polymer selected from the group consisting of styrenic block copolymers, ethylene/α-olefin interpolymers, interpolymers of ethylene, and mixtures thereof; and
c) from about 10% by weight to about 90% by weight of at least one tackifier
said adhesive composition, when in the form of a 1 mil thick film traveling at a speed of from about 300 feet per minute to about 500 feet per minute, cures upon exposure to radiation from H bulbs of two 600 watt per inch lamps.

31. A radiation curable hot melt adhesive composition comprising:
a) from about 10% by weight to about 40% by weight block copolymer having at least two blocks wherein the first block is a polyvinyl aromatic block and the second block is a polydiene block having vinyl functionality;
b) from about 5% by weight to about 40% by weight of at least one second polymer selected from the group consisting of styrenic block copolymers, ethylene/α-olefin interpolymers, interpolymers of ethylene, and mixtures thereof; and
c) from about 10% by weight to about 90% by weight of at least one tackifier,
said adhesive composition, when in the form of a 1 mil thick film, cures upon exposure to radiant energy of from about 25 $mJ/cm^2$ to about 200 $mJ/cm^2$.

32. The adhesive composition of claim 31, wherein said adhesive composition, when in the form of a 1 mil thick film, cures upon exposure to radiant energy of from about 40 $mJ/cm^2$ to about 200 $mJ/cm^2$.

33. The adhesive composition of claim 1, wherein said adhesive composition, when in the form of a 1 mil thick film traveling at a speed of from about 300 feet per minute to about 500 feet per minute, cures upon exposure to radiation from H bulbs of two 600 watt lamps.

34. The adhesive composition of claim 1, wherein said adhesive composition, when in the form of a 1 mil thick film, cures upon exposure to radiant energy of from about 25 $mJ/cm^2$ to about 200 $mJ/cm^2$.

35. The adhesive composition of claim 1, wherein said adhesive composition, when in the form of a 1 mil thick film, cures upon exposure to radiant energy of from about 40 $mJ/cm^2$ to about 200 $mJ/cm^2$.

36. The adhesive composition of claim 1, wherein said adhesive composition, when in the form of a 1 mil thick film, cures upon exposure to radiant 2 Mrads to 10 Mrads of electronic beam radiation.

37. The adhesive composition of claim 1, further comprising a tackifying agent that is liquid at about 25° C.

38. The adhesive composition of claim 1, further comprising a plasticizer that is liquid at about 25° C.

39. A radiation curable hot melt adhesive composition comprising:
a) from about 10% by weight to about 40% by weight block copolymer having at least two blocks wherein the first block is a polyvinyl aromatic block and the second block is a polydiene block having vinyl functionality;
b) from about 5% by weight to about 40% by weight of at least one second polymer selected from the group consisting of styrenic block copolymers, ethylene/α-olefin interpolymers, interpolymers of ethylene, and mixtures thereof; and
c) from about 10% by weight to about 90% by weight of at least one tackifier
said adhesive composition, when in the form of a 1 mil thick film, cures upon exposure to radiation from an H bulb of a 600 watt per inch lamp while traveling at a speed of 50 feet per minute.

40. A medical device having an adhesive composition of claim 1 that is intended to contact skin.

41. A medical device having an adhesive composition of claim 1 that is intended to contact skin.

42. A disposable article having at least one substrate bonded with an adhesive composition of claim 39, wherein said adhesive composition is in contact with an oil-based ingredient.

43. A disposable article having at least one substrate bonded with an adhesive composition of claim 11, wherein said adhesive composition is in contact with an oil-based ingredient.

* * * * *